(12) United States Patent
Su

(10) Patent No.: US 10,821,019 B2
(45) Date of Patent: Nov. 3, 2020

(54) URINE COLLECTOR

(71) Applicant: Sophia Hai Yun Su, North Point (HK)

(72) Inventor: Sophia Hai Yun Su, North Point (HK)

(*) Notice: Subject to any disclaimer, the term of this patent is extended or adjusted under 35 U.S.C. 154(b) by 142 days.

(21) Appl. No.: 15/920,406

(22) Filed: Mar. 13, 2018

(65) Prior Publication Data
US 2018/0200101 A1    Jul. 19, 2018

Related U.S. Application Data

(63) Continuation-in-part of application No. 14/673,784, filed on Mar. 30, 2015, now abandoned, which is a continuation-in-part of application No. 14/670,399, filed on Mar. 26, 2015, now abandoned.

(51) Int. Cl.
*A61F 5/44* (2006.01)
*A61F 5/455* (2006.01)

(52) U.S. Cl.
CPC ............ *A61F 5/4405* (2013.01); *A61F 5/455* (2013.01)

(58) Field of Classification Search
CPC ....................................................... A61F 5/455
USPC .......................................... 4/455, 456, 144.1
See application file for complete search history.

(56) References Cited

U.S. PATENT DOCUMENTS

| | | | | |
|---|---|---|---|---|
| 380,473 A | * | 4/1888 | Duffey ................... | A47B 73/00 211/74 |
| 633,004 A | * | 9/1899 | Hogan ................... | A61G 9/003 4/456 |
| 682,680 A | * | 9/1901 | Thornton ................. | A47K 5/10 222/181.2 |
| 2,567,830 A | * | 9/1951 | Timian ................... | A61G 9/003 4/455 |
| 2,955,294 A | * | 10/1960 | Silverstein ........... | A61G 7/1009 4/456 |
| 3,514,793 A | * | 6/1970 | West ..................... | A47C 15/006 4/456 |
| 5,848,443 A | * | 12/1998 | Waugh .................... | B60R 15/04 4/458 |
| 6,079,058 A | * | 6/2000 | Green .................. | A47K 11/045 4/479 |

* cited by examiner

*Primary Examiner* — Lauren A Crane
(74) *Attorney, Agent, or Firm* — Raymond Y. Chan; David and Raymond Patent Firm

(57) ABSTRACT

A urine collector for collecting urine for a user includes a basin which includes a collector including a bottom wall and a surrounding wall upwardly extended therefrom to define a cavity and a top opening, and a top cover supported on the top opening of the collector; and a urine guider provided at the bottom wall of the collector for collecting urine at a peripheral portion thereof for collecting the urine at the urine guider within the cavity of the collector, wherein the bottom wall of the collector further includes an enlarge bottom base defining a circular guiding slot, and an inner concave guiding bottom extended inward and upward from the enlarge bottom base, so that the enlarge bottom base enhances a stabilization of the collector, wherein the urine guider is provided at the inner concave guiding bottom.

8 Claims, 12 Drawing Sheets

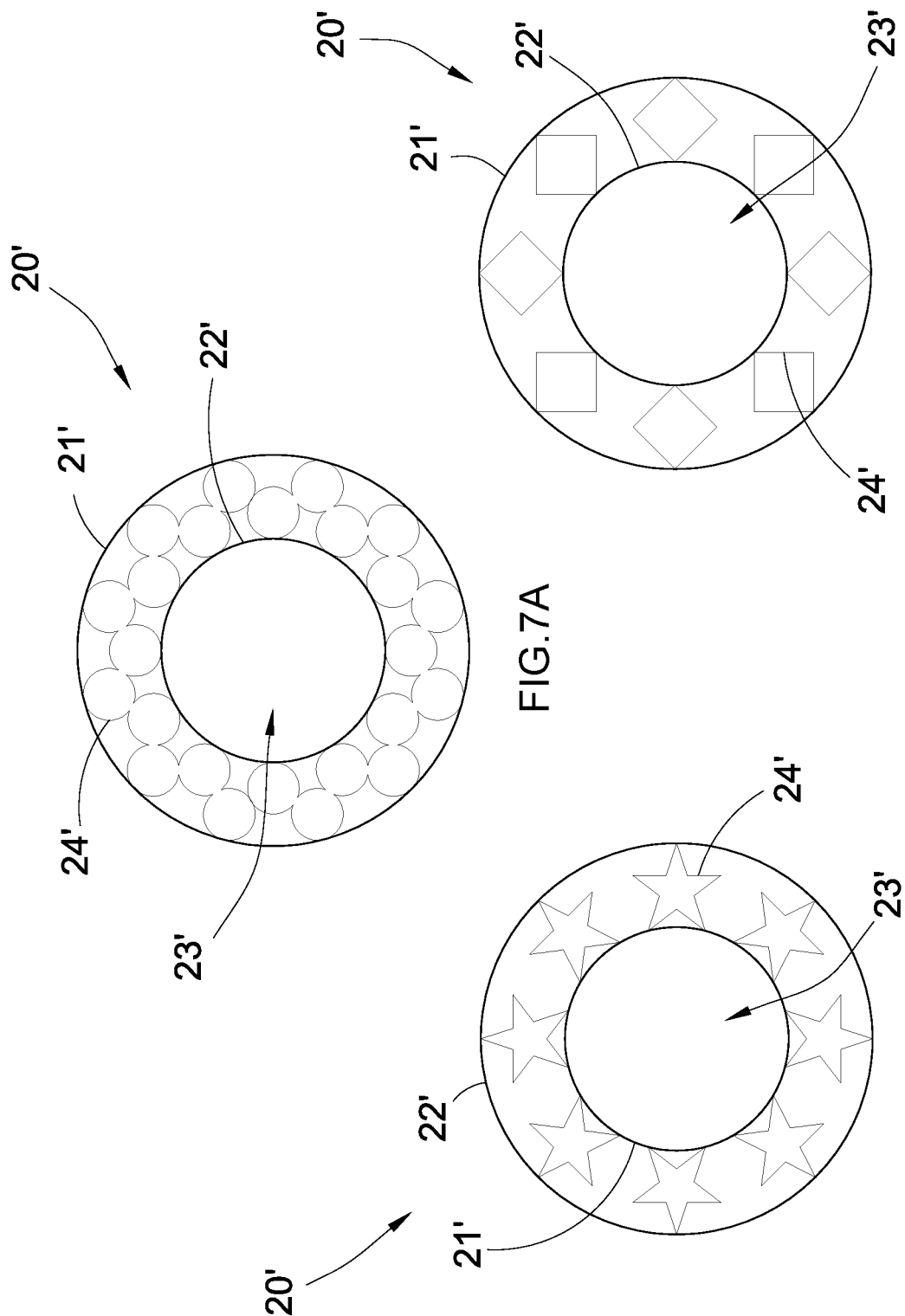

URINE COLLECTOR

CROSS REFERENCE OF RELATED APPLICATION

This is a Continuation-In-Part application that claims the benefit of priority under 35 U.S.C. § 120 to a non-provisional application, application Ser. No. 14/673,784, filed Mar. 30, 2015.

NOTICE OF COPYRIGHT

A portion of the disclosure of this patent document contains material which is subject to copyright protection. The copyright owner has no objection to any reproduction by anyone of the patent disclosure, as it appears in the United States Patent and Trademark Office patent files or records, but otherwise reserves all copyright rights whatsoever.

BACKGROUND OF THE PRESENT INVENTION

Field of Invention

The present invention relates to a health care product, and more particularly to a urine collector for special patients who are not easy to move around such as vertebral fracture patients, bone fracture patients, apoplexy patients and obese patients.

DESCRIPTION OF RELATED ARTS

The use of a urinary collection device is well known to collect urine from a physically-disabled person. The urinary collection device can substantially reduce the workload for health care workers. Generally, a potty or a bed urinal is used as the urinary collection device to collect urine from the patient. To a physically-disabled patient, urination is a hardship to the patient or the patient family member or nurse who takes care the patient. Generally, such potty or bed urinal, which is relatively high to the patient, is used to collect urine from a physically-disabled person. It may require one or two people to assist the patient for each urination and it is really suffering to the patient. In other words, such conventional urinary collection devices are difficult to use for urine collection and urine always leaks between the contacting surface of the urinary collection device and the body of the patient. Bed linens and clothing are contaminated due to the urine leakage, so as to cause different health problems such as infection or pressure ulcers.

An improved urine collector is a simple, comfortable to wear, effective, and convenience appliance to take care of the bedridden patients, wherein the improved urine collector can reduce workloads for nurses and families. In other words, the conventional urine collector can help the care workers and/or patient's family members to reduce the stress for caring the bedridden patients.

An improved urine collector for bedridden patients to solve the common problems of the current urine collectors can only cover on the meatus urinarius of the patient, the improved urine collector is difficult to collect all discharging urine from the patients. As a result, bed linens and clothing are easily to be contaminated by the urine. In addition, physically-disabled patients with low limb fracture, pelvic fracture, or postpartum are difficult to use the above mentioned urine collectors because they are not powerful enough to retain the urine collector in position. An improper use of urine collector may cause serious injuries due to the excessive movement of the patients.

SUMMARY OF THE PRESENT INVENTION

An object of the present invention is to provide a urine collector for special patients who are not easy to move around such as vertebral fracture patients, bone fracture patients, apoplexy patients and obese patients.

Another object of the present invention is to provide a urine collector which is stable enough to stand and to prevent from being overturned.

Another object of the present invention is to provide a urine collector which is stable and also has a thin and portable structure.

Another object of the present invention is to provide a urine collector which has a good cushioning effect, so that the continuous and overnight urine of patients will not spill over from the urine collector.

Another object of the present invention is to provide a urine collector which can keep dry and comfortable to prevent bedsore.

Another object of the present invention is to provide a urine collector which is suitable to be used on both the soft and the hard mattress, thereby preventing the urine collector from sinking into the mattress.

Another object of the present invention is to provide a urine collector which is convenient to be cleaned.

Another object of the present invention is to provide a urine collector which has a smooth contacting surface, so that the sharp the corner angle is removed and the patients feel comfortable sitting on the urine collector.

Another object of the present invention is to provide a urine collector, wherein the urine collector is formed in a compact structure and is light in weight, such that the urine collector can be used by the patients for overnight. In other words, health care workers do not need to frequently unload the urine in the urine collector of the present invention.

Another object of the present invention is to provide a urine collector which has a relatively thinner structure and can discharge urine continuously.

Another object of the present invention is to provide a urine collector which is adapted to collect urine throughout the hip area but not limiting to the urination portion, so as to prevent leaking out of urine. In addition, a top side a top cover of the collector of the urine collector is inclinedly extended from an outer peripheral edge toward a center, so as to ensure and guide all the urine be collected toward a container through a top opening of the collector to avoid splashing and leakage. Since the collector is not used to store urine being collected but to function as a transition means to continue to guide the container, the collector can be constructed in compact size with a thinner thickness and a lighter weight that enables an overnight usage without the need to replace the collector. Accordingly, to a less severe patient, the patient can place the collector in position by himself or herself and there is no need to have anyone to help for urination. To a more severe patient, it simply needs someone to slight support the hip of the patient to place the collector in position for urination that substantially alleviates suffering to the patient and reduces burden of the care for the patient. For hospitals or senior care facilities, the collector can be directly connected to the sewage drain system that links to a urine collection container for ease of filtration or disinfection treatment, so that the present invention can save a lot of manpower and meet the environmental health requirement.

According to the present invention, the foregoing and other objects and advantages are attained by a urine collector, comprising:

a urine guider provided at the bottom wall of the collector for collecting urine at a peripheral portion thereof for collecting the urine at the urine guider within the cavity of the collector, wherein the bottom wall of the collector further comprises an enlarge bottom base defining a circular guiding slot, and an inner concave guiding bottom extended inward and upward from the enlarge bottom base, so that the enlarge bottom base enhances a stabilization of the collector, wherein the urine guider is provided at the inner concave guiding bottom.

According to the present invention, the foregoing and other objects and advantages are also attained by a urine collector, comprising a collector, a transporting tube, and a container. The transporting tube can be a PET tube, a latex tube, or a silica gel tube. The collector is pot-shaped container having a top opening, and is preferably made of hard plastic, foam material, or hard rubber. The urine collector further comprises a ring-shaped top cover coupled on a top edge of the collector, wherein the top cover is preferably made of plastic or latex, and is obliquely extended toward a center of the top cover, such that a top side of the top cover is slanted and downwardly extended toward the top opening of the collector. The urine collector further comprises a guider and a discharging unit arranged on a bottom portion of the collector, wherein a top side of the guider is lower than a bottom surface of the collector. In addition, the collector has a surrounding sidewall, wherein the surrounding sidewall can be a straight wall, an obliquely and downward-extended arc-shaped wall, or an inclined straight wall. It is worth mentioning that the collector also can be made of metal or wood.

Accordingly, the discharging unit comprises a collecting port and a discharging port located on an inner wall of the transporting tube, wherein the collecting port is operatively communicated with the guider and the discharging port is operatively linked with the transporting tube. The collecting port and the discharging port are operatively connected with each other.

Accordingly, the hip portion of the patient sits on the collector that the collector will cover the urethra of the patient so as to prevent the leakage of the urine, wherein the collector serves as a temporary collector for guiding the urine flowing into the container, such that the urine collector can be used for urine without frequently discharging urine in the collector.

Accordingly, the container is not limited to a container with or without scale and a sewage drain and the like.

The present invention is simple in structure, light in weight, and easy to operate, such that the present invention has benefits for the bedridden patients for clinical care and home care, and it is also convenient for the bedridden patients to solve their urinating problems by themselves who cannot get to a restroom to urinate in a convenience and privacy manner. At the same time, the ring-shaped top cover is preferably made of latex, which is very comfortable for the user to sit on, and the ring-shaped top cover is slightly tilted towards a center thereof to ensure the discharging urine flowing into the collector. The shape of the guider and the surrounding sidewall are able to facilitate the discharging urine flowing into the collector, such that the urine can be effectively discharged from the collector to the container, so as to reduce the leakage of urine for contaminating the bedding, and further reduce the incidence of the ulcers.

Additional advantages and features of the invention will become apparent from the description which follows, and may be realized by means of the instrumentalities and combinations particular point out in the appended claims.

Still further objects and advantages will become apparent from a consideration of the ensuing description and drawings.

These and other objectives, features, and advantages of the present invention will become apparent from the following detailed description, the accompanying drawings, and the appended claims.

BRIEF DESCRIPTION OF THE DRAWINGS

FIG. 7A-7C illustrate different configurations of the urine directing grooves of the urine collector according to the second preferred embodiment of the present invention.

DETAILED DESCRIPTION OF THE PREFERRED EMBODIMENT

The following description is disclosed to enable any person skilled in the art to make and use the present invention. Preferred embodiments are provided in the following description only as examples and modifications will be apparent to those skilled in the art. The general principles defined in the following description would be applied to other embodiments, alternatives, modifications, equivalents, and applications without departing from the spirit and scope of the present invention.

Figure 1:
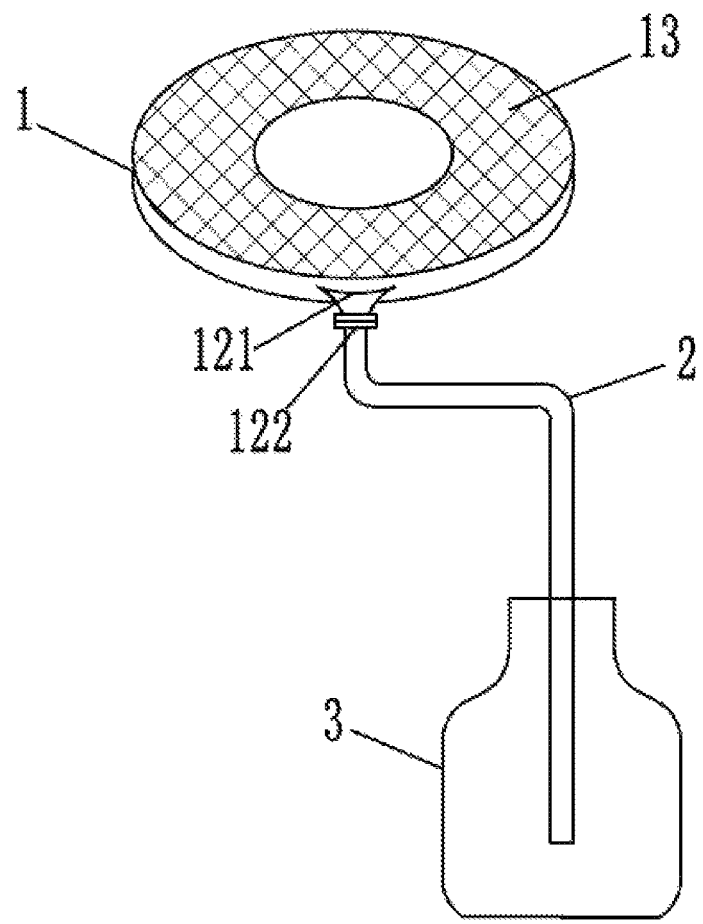
FIG. 1 is a perspective view of a urine collector according to a preferred embodiment of the present invention.
Figure 2:
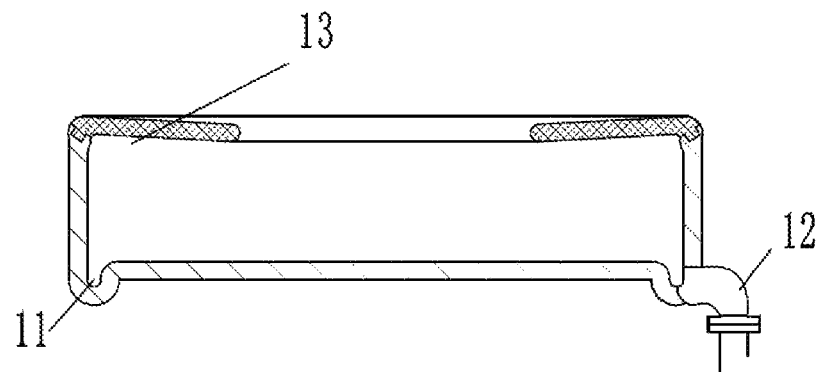
FIG. 2 is a sectional view of the urine collector according to the above preferred embodiment of the present invention.

Referring to FIGS. 1 and 2 of the drawings, a urine collector according to a preferred embodiment of the present invention is illustrated, wherein the urine collector comprises a collector 1 having a top opening and a cavity, a transporting tube 2, which is made of PET material, connected to the collector 1 for transporting the urine, and a container 3 operatively connected with the transporting tube 2 for containing the urine from the collector 1 through the transporting tube 2. The collector 1 is a pot-shaped collector and made of a rigid plastic material. Accordingly, the collector 1 comprises a urine guider 11 provided at a bottom portion of the collector 1 for guiding urine at the urine guider 11 within the cavity, and a discharging unit 12 operatively connected with the urine guider 11 of the collector 1, wherein the urine guider 11 is a guiding groove indented around a peripheral portion of the bottom wall of the collector 1. It is worth mentioning that a top portion of the urine guider 11 is lower than the bottom wall of the collector 1. And, the collector 1 further comprises a surrounding wall, wherein the surrounding wall is a vertical wall extended with respect to the bottom wall of the collector 1 that the size of the top opening of the collector 1 matches the size of the bottom side of the collector 1. In other words, the urine guider 11 is formed between the surrounding wall and the bottom wall of the collector 1.

Moreover, the collector 1 further comprises a ring-shaped top cover 13 coaxially coupled on a top edge of the collector 1 to partially cover the top opening thereof, wherein the top cover 13 is preferably made of latex. A top side of the top cover 13 is inclinedly extended from an outer peripheral edge toward a center, so as to extend toward the top opening of the collector 1 to guide the urine toward the container 1 through the top opening thereof. In other words, the slope of the top side of the top cover 13 is gradually decreased from an outer edge of the top cover 13 to an inner edge thereof. Furthermore, the discharging unit 12 comprises a collecting port 121 located at the surrounding wall of the container 1 and a discharging port 122, wherein the collecting port 121 is operatively linked with the urine guider 11 and the discharging port 122 is operatively linked with the transporting tube 2, and the collecting port 121 and the discharging port 122 are operatively connected with each other. The discharging port 122 is connected to the inner wall of the transporting tube 2. In other words, the urine moves along the guider 11 to reach the collecting port 121, and passes through the collecting port 121 and the discharging port 122 respectively, so as to reach the transporting tube 2, and then the urine moves along the transporting tube 2 to be guide into the container 3.

Accordingly, the collector 1 is placed below a hip of the patient, especially female patient, wherein the collector serves as a temporary collecting station for guiding the urine to flow into the container 3.

Figure 3:
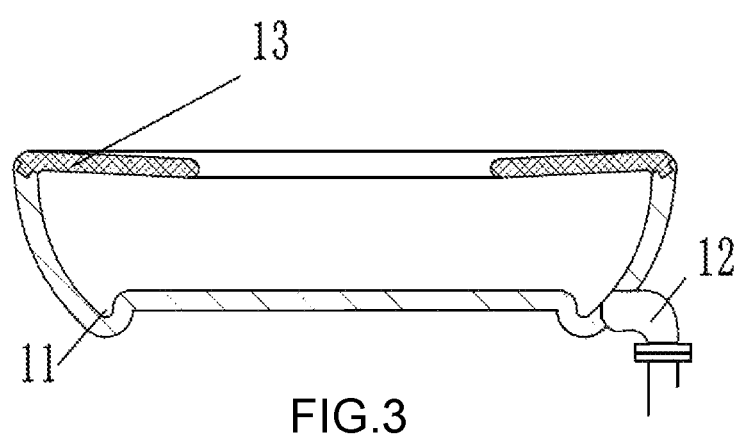
FIG. 3 illustrates a first alternative mode of the collector of the urine collector according to the above preferred embodiment of the present invention, illustrating the arc-shaped wall of the collector.

FIG. 3 illustrates a first alternative mode the urine collector, wherein the urine collector comprises a collector 1 having a top opening and a cavity, a transporting tube 2, which is made of latex material, connected to the collector 1 for transporting the urine, and a container 3 operatively connected with the transporting tube 2 for containing the urine from the collector 1 through the transporting tube 2. The collector 1 is a pot-shaped collector and made of a rigid rubber material. Accordingly, the collector 1 comprises a urine guider 11 provided at a bottom portion of the collector 1 for guiding urine at the urine guider 11 within the cavity, and a discharging unit 12 operatively connected with the urine guider 11 of the collector 1, wherein the urine guider 11 is a guiding groove indented around a peripheral portion of the bottom wall of the collector 1. It is worth mentioning that a top portion of the urine guider 11 is lower than the bottom wall of the collector 1. And, the collector 1 further comprises a surrounding wall, wherein the surrounding wall is an arc-shaped wall extended with respect to the bottom wall of the collector 1 that the size of the top opening of the collector 1 is larger than the size of the bottom wall of the collector 1. In other words, the urine guider 11 is formed between the surrounding wall and the bottom wall of the collector 1.

Moreover, the collector 1 further comprises a ring-shaped top cover 13 coaxially coupled on a top edge of the collector 1 to partially cover the top opening thereof, wherein the top cover 13 is preferably made of latex. A top side of the top cover 13 is inclinedly extended from an outer peripheral edge toward a center, so as to extend toward the top opening of the collector 1 to guide the urine toward the container 1 through the top opening thereof. In other words, the slope of the top side of the top cover 13 is gradually decreased from an outer edge of the top cover 13 to an inner edge thereof. Furthermore, the discharging unit 12 comprises a collecting port 121 located at the surrounding wall of the container 1 and a discharging port 122, wherein the collecting port 121 is operatively linked with the urine guider 11 and the discharging port 122 is operatively linked with the transporting tube 2, and the collecting port 121 and the discharging port 122 are operatively connected with each other. The discharging port 122 is connected to the outer wall of the transporting tube 2. In other words, the urine moves along the guider 11 to reach the collecting port 121, and passes through the collecting port 121 and the discharging port 122 respectively, so as to reach the transporting tube 2, and then the urine moves along the transporting tube 2 to be guide into the container 3.

Accordingly, the collector 1 is placed below a hip of the patient, especially female patient, wherein the collector serves as a temporary collecting station for guiding the urine to flow into the container 3.

Figure 4:
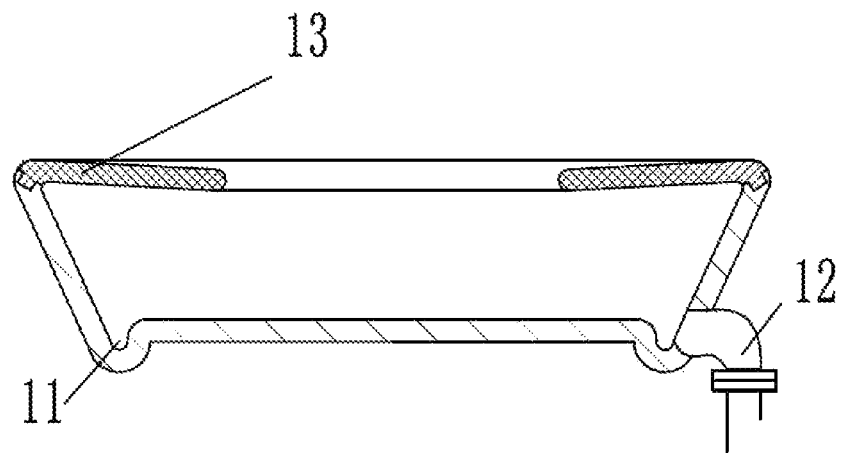
FIG. 4 illustrates a second alternative mode of the collector of the urine collector according to the above preferred embodiment of the present invention, illustrating the inclined wall of the collector.

FIG. 4 illustrates a second alternative mode the urine collector, wherein the urine collector comprises a collector 1 having a top opening and a cavity, a transporting tube 2, which is made of polycarbonate material, connected to the collector 1 for transporting the urine, and a container 3 operatively connected with the transporting tube 2 for containing the urine from the collector 1 through the transporting tube 2. The collector 1 is a pot-shaped collector and made of a rigid rubber material. Accordingly, the collector 1 comprises a urine guider 11 provided at a bottom portion of the collector 1 for guiding urine at the urine guider 11 within the cavity, and a discharging unit 12 operatively connected with the urine guider 11 of the collector 1, wherein the urine guider 11 is a guiding groove indented around a peripheral portion of the bottom wall of the collector 1. It is worth mentioning that a top portion of the urine guider 11 is lower than the bottom wall of the collector 1. And, the collector 1 further comprises a surrounding wall, wherein the surrounding wall is an inclined wall extended with respect to the bottom wall of the collector 1 that the size of the container 1 is gradually reduced from the top opening of the collector 1 to the bottom wall of the collector 1. In other words, the urine guider 11 is formed between the surrounding wall and the bottom wall of the collector 1.

Moreover, the collector 1 further comprises a ring-shaped top cover 13 coaxially coupled on a top edge of the collector 1 to partially cover the top opening thereof, wherein the top cover 13 is preferably made of latex. A top side of the top cover 13 is inclinedly extended from an outer peripheral edge toward a center, so as to extend toward the top opening of the collector 1 to guide the urine toward the container 1 through the top opening thereof. In other words, the slope of the top side of the top cover 13 is gradually decreased from an outer edge of the top cover 13 to an inner edge thereof. Furthermore, the discharging unit 12 comprises a collecting port 121 located at the surrounding wall of the container 1 and a discharging port 122, wherein the collecting port 121 is operatively linked with the urine guider 11 and the discharging port 122 is operatively linked with the transporting tube 2, and the collecting port 121 and the discharging port 122 are operatively connected with each other. The discharging port 122 is connected to the outer wall of the transporting tube 2. In other words, the urine moves along the guider 11 to reach the collecting port 121, and passes through the collecting port 121 and the discharging port 122 respectively, so as to reach the transporting tube 2, and then the urine moves along the transporting tube 2 to be guide into the container 3.

Accordingly, the collector 1 is placed below a hip of the patient, especially female patient, wherein the collector serves as a temporary collecting station for guiding the urine to flow into the container 3.

Figure 5:
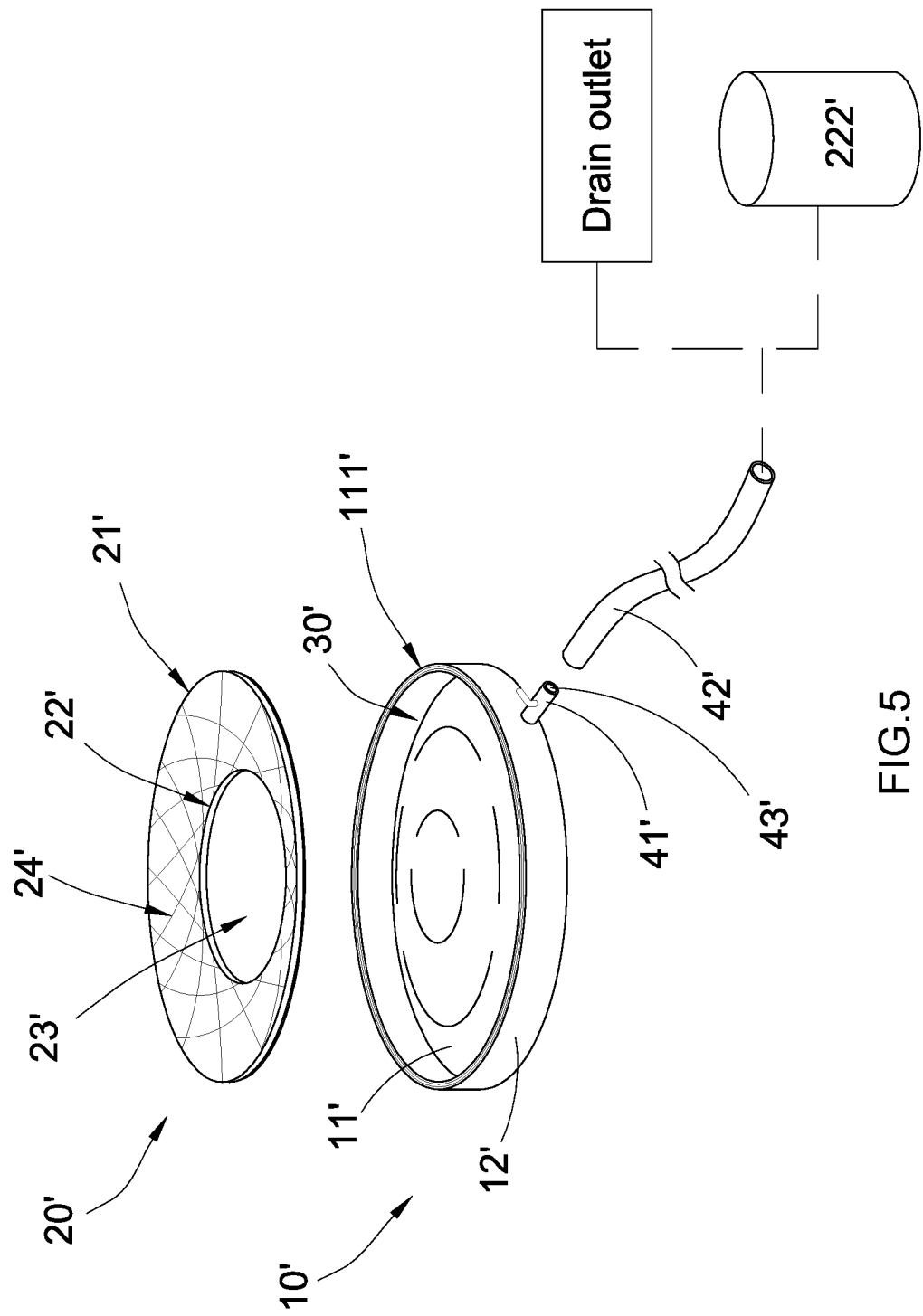
FIG. 5 is a perspective view of a urine collector according to a second preferred embodiment of the present invention.
Figure 6:
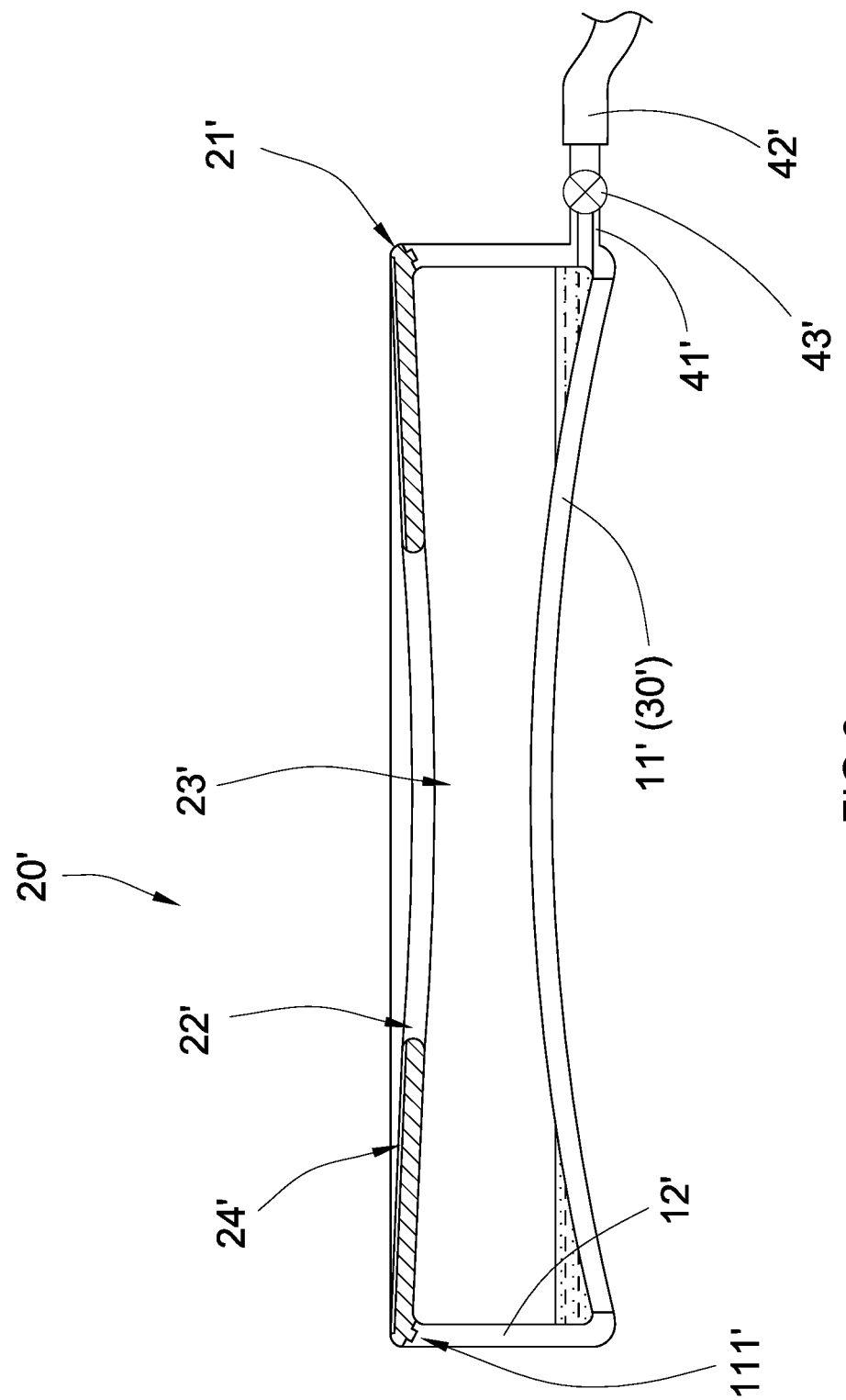
FIG. 6 is a sectional view of the urine collector according to the second preferred embodiment of the present invention.

As shown in FIG. 5, a urine collector according to a second embodiment illustrates an alternative mode of the first embodiment, wherein the urine collector is arranged for collecting urine from a user, especially a female user. As shown in FIGS. 5 and 6, the urine collector comprises a basin which comprises a collector 10' and a top cover 20', and a urine guider 30'.

Accordingly, the basin has a cavity for collecting urine, a top side having a size adapted for covering a hip of the user, and a top opening formed at the top side to communicate with the cavity. The basin is arranged for being placed underneath the hip of the user, such that the top side of the basin is large enough to cover the urethra of the user to prevent the leakage of the urine. Preferably, the user is able to sit on the top side of the basin to collect the urine in the cavity through the top opening. In addition, the top opening of the basin is large enough to cover the urethra of the user.

The collector 10' has a bottom wall 11' and a surrounding wall 12' upwardly extended from the bottom wall 11' to define the cavity within the bottom wall 11' and the surrounding wall 12'. Accordingly, the collector 10' is a shallow pan configuration that the collector 10' can be slid underneath the hip of the user. Preferably, the depth of the cavity, i.e. the height of the surrounding wall 12', is about one inch deep. The collector 10' is preferably configured to have a circular shape. It is appreciated that the collector 10' can be formed in oval shape or irregular shape. The bottom wall 11' of the collector 10' can be a flat bottom wall.

The top cover 20' is detachably supported on top of the collector 10', wherein the top cover 20' has a ring shape defining an outer peripheral edge 21', an inner peripheral edge 22', and a through hole 23' within the inner peripheral edge 22'. The top opening of the basin is defined at the through hole 23' of the top cover 20' and the top side of the basin is defined at the top side of the top cover 20'.

Accordingly, the outer peripheral edge 21' of the top cover 20' is detachably coupled at the surrounding wall 12' of the collector 10'. Preferably, a coupling slot 111' is formed at a top edge of the surrounding wall 12' of the collector 10', wherein the outer peripheral edge 21' of the top cover 20' is detachably coupled at the coupling slot 111' of the collector 10'. It is worth mentioning that the surrounding wall 12' of the collector 10' can be configured to have a vertical wall, an arc-shaped wall, or an inclined wall as mentioned in the first embodiment.

As shown in FIG. 6, the top side of the top cover 20' is sloped downwardly from the outer peripheral edge 21' of the top cover 20' to the inner peripheral edge 22' thereof for guiding the urine to flow into the collector 10'. In case the urine is spilled on the top cover 20', the slanted top side of the top cover 20' will guide the urine to flow toward the through hole 23' so as to collect the urine in the collector 10'.

In addition, the top cover 20' further has a plurality of urine directing grooves 24' indently formed on the top side of the top cover 20' and extended to the inner peripheral edge 22' thereof for guiding the urine to flow toward the through hole 23' of the top cover 20'. As shown in FIG. 5, the urine directing grooves 24' are grouped into a first groove set and a second groove set, wherein the first and second groove sets are intersected with each other. Preferably, the urine directing grooves 24' are elongated straight grooves radially extended toward the through hole 23' of the top cover 20'. It is worth mentioning that the urine directing grooves 24' can be configured to have different shapes and sizes, such as circular shape, star shape, or rectangular shape, on the top side of the top cover 20' to guide the flow of urine into the cavity, as shown in FIG. 7.

The urine guider 30' is provided at a bottom portion of the basin for collecting urine at the urine guider 30' within the cavity of the basin. In particular, the urine guider 30' is provided at the bottom wall 11' of the collector 10' at a peripheral portion thereof for collecting the urine at the urine guider 30' within the cavity of the basin so as to enhance a stabilization of the collector 10' after the urine is collected. It is worth mentioning that when the urine is collected in the cavity of the collector 10', the urine will be moved by the movement of the collector 10'. Therefore, the center of mass of the basin will be shifted, which may cause the basin to be flipped unintentionally. When the urine is collected at the urine guider 30' around the peripheral portion of the bottom wall 11' of the collector 10', the urine will be retained at the peripheral portion of the collector 10' by the weight force, such that the collector 10' can be stabilized to minimize the shifting of the center of mass due to the movement of the collector 10'.

As shown in FIG. 6, the urine guider 30' is integrated with the bottom wall 11' of the collector 10' that the bottom wall 11' is a convex wall radially sloping down toward the peripheral portion for collecting the urine at the peripheral portion of the collector 10' so as to enhance a stabilization of the collector 10' after the urine is collected. It is appreciated that the urine guider 30' can be configured to have a guiding groove indentedly formed at the peripheral portion of the bottom wall 11' of the collector 10', as mentioned in the first embodiment, for collecting the urine at the peripheral portion of the collector 10' so as to enhance a stabilization of the collector 10' after the urine is collected.

The urine collector further comprises a discharging unit 40' operatively connected with the urine guider 30' for discharging the urine therefrom, wherein the discharging unit 40' comprises a discharging port 41' formed at the basin to communicate with the urine guider 30' and a transporting tube 42' detachably coupled at the discharging port 41' for discharging the urine at the urine guider 30' through the discharging port 41'.

As shown in FIG. 6, the discharging port 41' is through slot formed at the surrounding wall 12' of the collector 10' at the lower portion thereof to communicate with the urine guider 30'. Preferably, the discharging unit 40' further comprises a discharging valve 43' coupled at the discharging port 41', such that the discharging valve 43' is selectively opened for discharging urine from the urine guider 30' and closed for retaining urine at the urine guider 30'. It is worth mentioning that the discharging port 41' is formed at the surrounding wall 12' of the collector 10', such that the bottom wall 11' of the collector 10' can be stably placed on a supporting surface, such as bed surface.

The discharging unit 40' further comprises a container 44' detachably linked to the transporting tube 42' for collecting urine from the urine guider 30' through the transporting tube 42'. Accordingly, the transporting tube 42' has one end detachably coupled at the discharging port 41' and an opposed end detachably coupled to the container 44'. Therefore, once the discharging valve 43' is opened, the urine at the urine guider 30' will be discharged to the container 44' through the transporting tube 42'. It is worth mentioning that the transporting tube 42' can be extended to a drain outlet to directly discharge the urine to the drain outlet without the container 44'.

In order to use the urine collector of the present invention, the user is able to place the basin under the hip of the user, wherein the user is able to sit on top of the basin to align the urethra of the user within the top opening of the basin. As a result, the urine will be temporary stored at the urine guider 30' and will then be guided to discharge to the container 44'. Depending on the volume of the container 44', the user is able to re-use the basin for a relatively long period of time, such as overnight, without directly draining the urine out of the basin manually, so as to reduce the workload of the healthcare worker or family member. It is worth mentioning that the urine collector can be cleaned by directly pouring clean water into the cavity of the collector 10' through the top opening to rinse the entire urine collector and discharging the water from the collector 10' to the container 30'.

According to the above mentioned embodiments and their alternatives, the collector 1, 10' can be made of polymer materials, such as rigid plastic, rigid rubber, or polycarbonate materials. In other words, since the collector 1, 10' is made of light in weight materials, the collector 1, 10' is easy to be carried, and it is convenient for the patients to use. In addition, the transporting tube 2, 42' of the embodiments and their alternatives can be made of PET, silica gel, and latex, such that the above mentioned materials are light in weight and are durable.

In view of above embodiments, the urine collector of the present invention is constructed in a compact structure that has a relatively thinner structure and a light weight, such that the urine collector can discharge urine continuously and be used by the patients for overnight. In other words, health care workers do not need to frequently unload the urine in the urine collector of the present invention.

In addition, the urine collector of the present invention is adapted to collect urine throughout the hip area but not limiting to the urination portion, so as to prevent leaking out of urine. Also, a top side a top cover of the collector of the urine collector is inclinedly extended from an outer peripheral edge toward a center, so as to ensure and guide all the urine be collected toward a container through a top opening of the collector to avoid splashing and leakage. Since the collector is not used to store urine being collected but to function as a transition means to continue to guide the container, the collector can be constructed in compact size with a thinner thickness and a lighter weight that enables an overnight usage without the need to replace the collector. Accordingly, to a less severe patient, the patient can place the collector in position by himself or herself and there is no need to have anyone to help for urination. To a more severe patient, it simply needs someone to slight support the hip of the patient to place the collector in position for urination that substantially alleviates suffering to the patient and reduces burden of the care for the patient. For hospitals or senior care facilities, the collector can be directly connected to the sewage drain system that links to a urine collection container for ease of filtration or disinfection treatment, so that the present invention can save a lot of manpower and meet the environmental health requirement.

It is worth mentioning that the urine collector of the present invention is suitable for all kinds of people to collect urine in bed, especially for post-partum women, seniors, people with problems of frequent urination or urinary incontinence, and injured and sick patients. It is a urine collector enabling people in bed to urinate without leakage and avoiding overflowing of urine. The present invention provides a simple structure and compact size that can be manufactured by inexpensive material and in low cost, especially good for mass production without using complicated and expensive production tools and machines, benefiting both the consumers and the manufacturers.

Figure 8A:
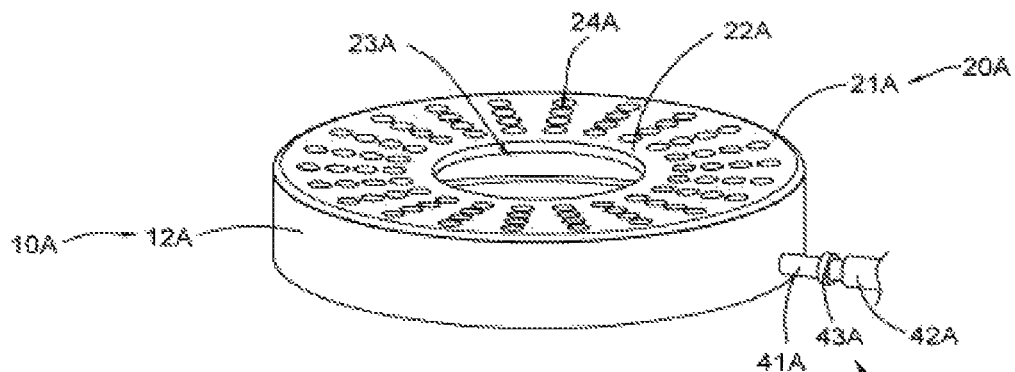
FIG. 8A is a perspective view of a urine collector according to a third preferred embodiment of the present invention.
Figure 8B:
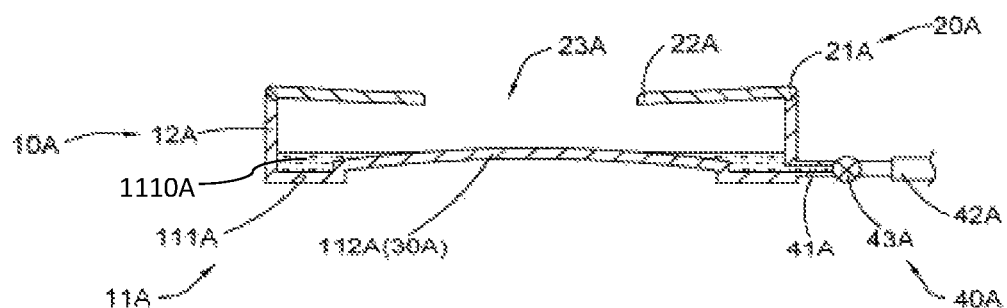
FIG. 8B is a perspective view of the urine collector according to the third preferred embodiment of the present invention.
Figure 9A:
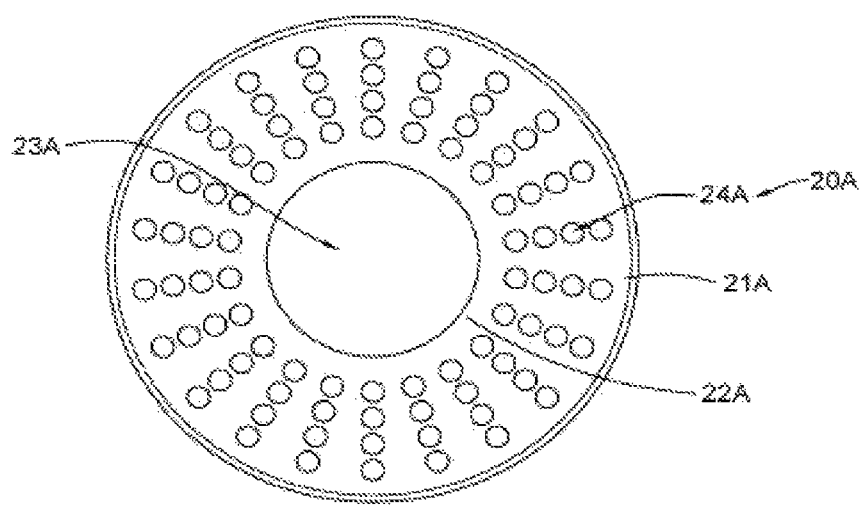
FIG. 9A is a perspective view of the urine collector according to the third preferred embodiment of the present invention.
Figure 9B:
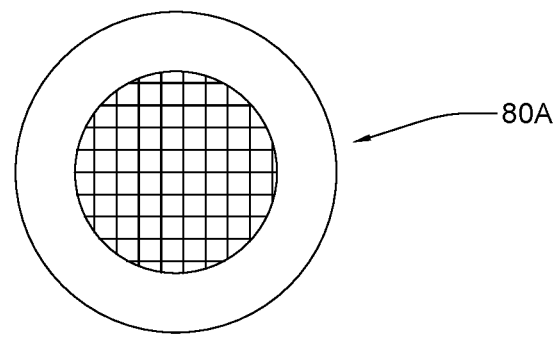
FIG. 9B is a perspective view of the urine collector according to the third preferred embodiment of the present invention.

Referring to FIG. 8A and FIG. 9B of the drawings, a urine collector according to a third embodiment illustrates an alternative mode of the first embodiment, wherein the urine collector is arranged for collecting urine for a user, especially for a special patient who is not easy to move around such as a vertebral fracture patient, a bone fracture patient, an apoplexy patients and obese patient. As shown in FIG. 8A to FIG. 9B of the drawings, the urine collector comprises a basin which comprises a collector 10A and a top cover 20A, and a urine guider 30A.

Accordingly, the basin has a cavity for collecting urine, a top side having a size adapted for covering a hip of the user, and a top opening formed at the top side to communicate with the cavity. The basin is arranged for being placed underneath the hip of the user, such that the top side of the basin is large enough to cover the urethra of the user to prevent the leakage of the urine. Preferably, the user is able to sit on the top side of the basin to collect the urine in the cavity through the top opening. In addition, the top opening of the basin is large enough to cover the urethra of the user.

The collector 10A comprises a bottom wall 11A and a surrounding wall 12A upwardly extended from the bottom wall 11A to define the cavity within the bottom wall 11A and the surrounding wall 12A. Accordingly, the collector 10A is a shallow pan configuration that the collector 10A can be slid underneath the hip of the user. Preferably, the collector 10A is preferably configured to have a circular shape. It is appreciated that the collector 10A can be formed in oval shape or irregular shape. The bottom wall 11A of the collector 10A can be a flat bottom wall.

Preferably, the collector 10A and the urine guider 30A are made of metallic material such as stainless steel. Compared with the urine collector according to the second embodiment, the urine collector of the second embodiment can be made of plastic and is portable to use, the urine collector of the third embodiment is steady. It is worth mentioning that the bottom wall 11A of the urine collector of the third embodiment further comprises an enlarge bottom base 111A defining a guiding slot 1110A, and an inner concave guiding bottom 112A extended inward and upward from the enlarge bottom base 111A, in such a manner that the urine on the inner concave guiding bottom 112A is guided to the enlarge bottom base 111A. In other words, the urine cannot largely remained on the inner concave guiding bottom 112A of the bottom wall 11A and is timely guided to the enlarge bottom base 111A, so that the collector 10A can be stabilized to minimize the shifting of the center of mass due to the movement of the collector 10 A.

The urine collector further comprises a discharging unit 40A operatively connected with the urine guider 30A for discharging the urine therefrom, wherein the discharging unit 40A comprises a discharging port 41A formed at the basin to communicate with the urine guider 30A and a transporting tube 42A detachably coupled at the discharging port 41A for discharging the urine at the urine guider 30A through the discharging port 41A. More specifically, the discharging port 41A is through slot formed at the surrounding wall 12A of the collector 10A at the lower portion thereof to communicate with the urine guider 30A. Preferably, the discharging unit 40A further comprises a discharging valve 43A coupled at the discharging port 41A, such that the discharging valve 43A is selectively opened for discharging urine from the urine guider 30A and closed for retaining urine at the urine guider 30A.

It is worth mentioning that the discharging port 41A is formed at the lower portion of the surrounding wall 12A of the collector 10A; furthermore, the bottom of the discharging port 41A and the bottom of the enlarge bottom base 111A are in the same horizontal surface; in such a manner that the enlarge bottom base 111A of the bottom wall 11A of the collector 10A can be stably placed on a supporting surface, and the urine cannot largely remained in the enlarge bottom base 111A of the bottom wall 11A and is timely guided to the discharging port 41A of the discharging unit 40A.

It is worth mentioning that the collector 10A and the urine guider 30A are large and flat enough to form a large pallet shape and are made of metallic material such that the urine collector is stable enough to stand and to prevent from being overturned. Moreover, the enlarge bottom base 111A of the bottom wall 11A has an large contacting area and the urine is timely guided to the discharging port 41A of the discharging unit 40A from the enlarge bottom base 111A of the bottom wall 11A, so that the urine collector has a good cushioning effect, so that the continuous and overnight urine of patients will not spill over from the urine collector. Moreover, the collector 10A and the urine guider 30A are stable enough to handle the overall hip portion of the patients and the top cover 20A, so that the urine has not leakage and spilling out problems, thereby solving the urinating problem of the special patients who are not easy to move around such as vertebral fracture patients, bone fracture patients, apoplexy patients and obese patients.

The top cover 20A is detachably supported on top of the collector 10A, wherein the top cover 20A has a ring shape defining an outer peripheral edge 21A, an inner peripheral edge 22A, and a through hole 23A within the inner peripheral edge 22A. The top opening of the basin is defined at the through hole 23A of the top cover 20A and the top side of the basin is defined at the top side of the top cover 20A. The top side of the top cover 20A is sloped downwardly from the outer peripheral edge 21A of the top cover 20A to the inner peripheral edge 22A thereof for guiding the urine to flow into the collector 10A. In case the urine is spilled on the top cover 20A, the slanted top side of the top cover 20A will guide the urine to flow toward the through hole 23A so as to collect the urine in the collector 10A. The top cover 20A is made of metal or plastic and is stabilized to support hips of patients.

Moreover, the top cover 20A further comprises a plurality of urine flow holes 24A evenly distributed on the top side of the top cover 20A and are evenly arranged between the outer peripheral edge 21A and the inner peripheral edge 22A. Preferably, the urine flow holes 24A are circular or square. In other embodiment, the urine flow holes 24A can also be configured to have different shapes and sizes, such as star shape or rectangular shape. In such a manner that the top cover 20A will guide the urine to flow toward the through hole 23A so as to collect the urine in the collector and the hip portion which is contacted with the top cover 20A can keep dry and comfortable to prevent bedsore. Moreover, the hip portion can easy to separate from the top cover 20A of the urine collector.

It is worth mentioning that the surrounding wall 12A of the collector 10A can be configured to have a vertical wall, an arc-shaped wall, or an inclined wall as mentioned in the first embodiment.

It is worth mentioning that preferably the urine collector in the second embodiment has a light and portable pan configuration and can be self-help used by general bedridden patient; while the urine collector in the third embodiment has a stable pan configuration and is especially suitable for the patients who are not easy to move around. It is worth mentioning that both of the urine collector in the second embodiment and in the third embodiment have thin configuration. For example, the height of the urine collector is only 2.0 cm to 2.5 cm. The patients only has to slightly raise his or her hip for using the urine, therefore, the urine collector is especially suitable for the unmovable patients.

It is worth mentioning that the urine collector in the third embodiment can be systematic used by the hospitals or the nursing home. For example, the urine collector can be installed in the sickbed and the urine can be guided through the transporting tube 42A to a uniform urine collection pool for unified disposal.

It is worth mentioning that the urine collector further comprises a urine isolating net 80A detachably attached on the center of the top cover 20A and over the through hole 23A. The urine isolating net 80A is able to isolate the urine and prevent the urine from splashing, thereby keeping cleaning and dry-touch. Preferably, the urine isolating net 80A is made of plastic and is disposable after use.

Figure 10:
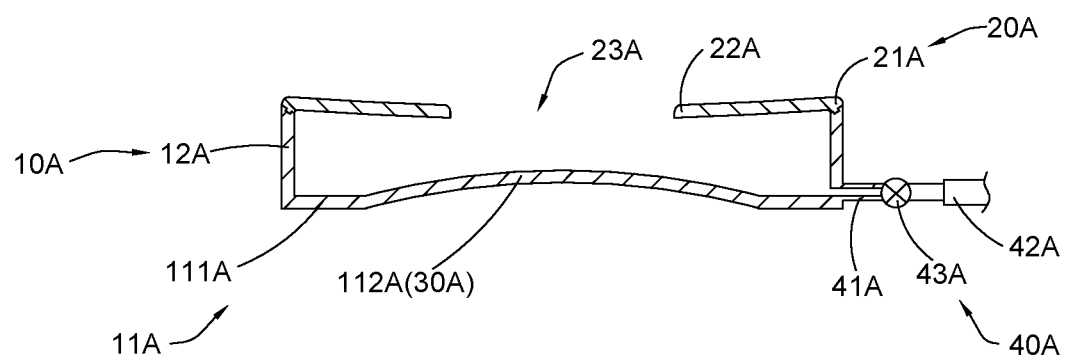
FIG. 10 is a perspective view of a urine collector illustrating an alternative mode of the third preferred embodiment of the present invention.

As shown in FIG. 10 of the drawings, a urine collector according to an alternative mode of the third embodiment of the present invention is illustrated. The urine collector of this alternative mode has a similar structure with the third embodiment as shown in FIG. 8 and FIG. 9. The main difference is the connection of the enlarge bottom base 111A and the inner concave guiding bottom 112A. Specifically, as shown in FIG. 8, the outer peripheral edge of the inner concave guiding bottom 112A is transversely and upwardly extended from the enlarge bottom base 111A; while as shown in FIG. 10 of the drawings, the outer peripheral edge of the inner concave guiding bottom 112A is directly and upwardly extended from the enlarge bottom base 111A. It is worth mentioning that the guiding slot 1110A defined by the enlarge bottom base 111A has a flat bottom. As the enlarge bottom base 111A has a support effect and has enough contacting area with the mattress, the urine collector is suitable to be used on both the soft and the hard mattress, thereby preventing the urine collector from sinking into the mattress.

Figure 11:
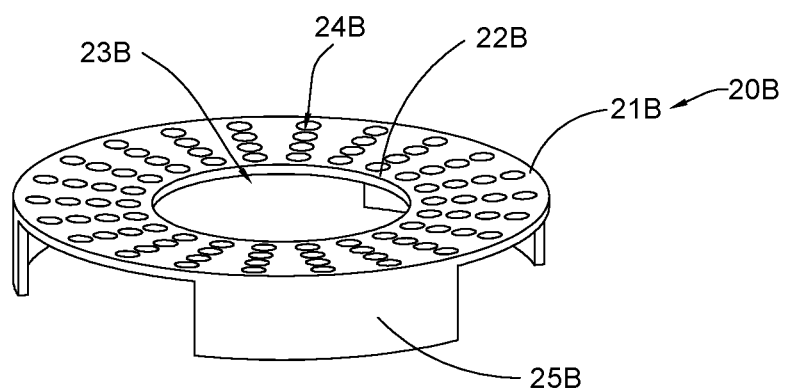
FIG. 11 is a perspective view of a urine collector according to a fourth preferred embodiment of the present invention.
Figure 12:
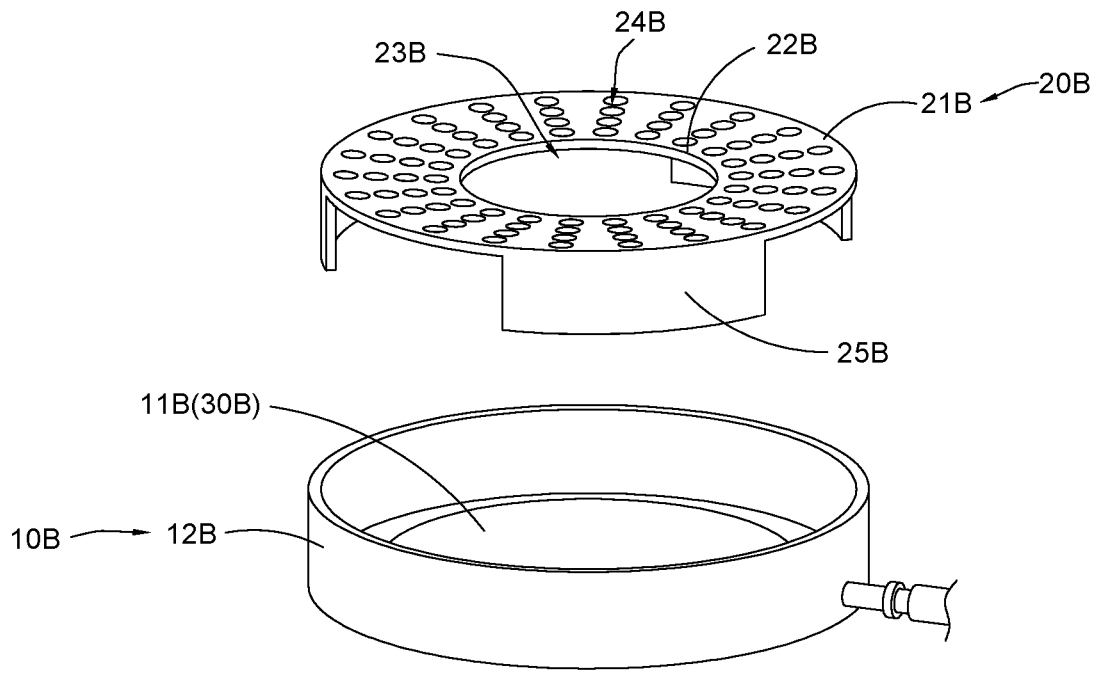
FIG. 12 is a perspective view of the urine collector according to the fourth preferred embodiment of the present invention.

Referring to FIG. 11 to FIG. 12 of the drawings, a urine collector according to a fourth embodiment illustrates an alternative mode of the first embodiment, wherein the urine collector is arranged for collecting urine for a user, especially for a special patient who is not easy to move around such as a vertebral fracture patient, a bone fracture patient, an apoplexy patients and obese patient. As shown in FIG. 11 to FIG. 12 of the drawings, the urine collector comprises a basin which comprises a collector 10B and a top cover 20B, and a urine guider 30B. The structures of the collector 10B and the urine guider 30B are similar to the structures thereof in the above embodiments. The main improvement is the structure of the top cover 20B.

Specifically, as shown in FIG. 11 to FIG. 12 of the drawings, the top cover 20B has a ring shape defining an outer peripheral edge 21B, an inner peripheral edge 22B, a through hole 23B within the inner peripheral edge 22B, and a plurality of urine flow holes 24B evenly arranged between the outer peripheral edge 21B and the inner peripheral edge 22B. The top cover 20B further comprises an extending support 25B extended downwardly along the surrounding wall 12B of the collector 10 from the outer peripheral edge 21B. The top opening of the basin is defined at the through hole 23B of the top cover 20B and the top side of the basin is defined at the top side of the top cover 20B. The diameter of the outer peripheral edge 21B of the top cover 20B is slight smaller than the diameter of the collector 10B. Preferably, in the fourth embodiment of the present invention, the extending support 25B of the top cover 20B has three extending support legs spaced arranged with each other. In other embodiment, the number of the extending supports 25B can be changed. Preferably, in the fourth embodiment of the present invention, when the top cover 20B is detachably supported on top of the collector 10B, the extending support 25B is arranged in the inner side of the collector 10B. However, in other embodiments, the extending support 25B can also be provided contacting with the outer side of the collector 10B. Therefore, the top cover 20B is stably coupled with the collector 10B and is not easy to be slipped out when the patient uses the urine collector. The top cover 20B is easy to be taken off from the collector 10B and is convenient to be cleaned.

The outer peripheral edge 21' of the top cover 20' is detachably coupled at the coupling slot 111' of the collector 10' as shown in FIG. 5. The connection method of the top cover 20' and the collector 10' is defined as embedding type. While the top cover 20B is detachable coupled with the collector 10B in a buckle covering type as shown in FIG. 11 to FIG. 12 of the drawings.

As some patients have to sit on the urine collector for a long time, the inclined top portion of the top cover 20B is thinness such as being made by 1 mm thickness steel disc with holes so as to reduce the rigidness and to improve comfort. The extending support 25B can widening and thickening to enhance the undertake force of the extending support 25B. In other embodiment, the inclined top portion of the top cover 20B is made of latex to improve comfort. In other embodiment, the extending support 25B can also made of latex with proper hardness so as to not only support inclined top portion of the top cover 20B but also to improve comfort.

Figure 13:
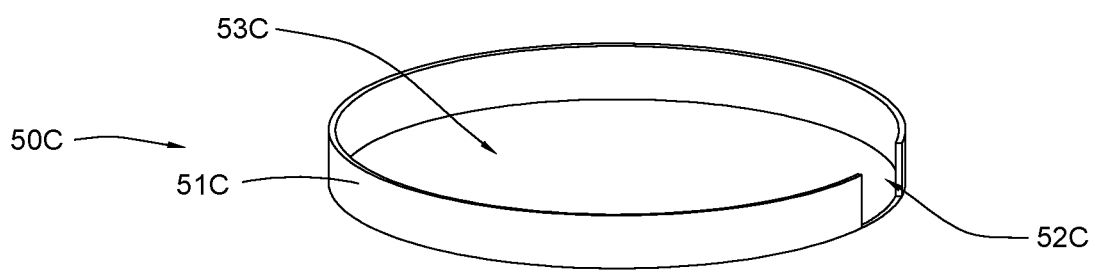
FIG. 13 is a perspective view of a urine collector according to a fifth preferred embodiment of the present invention.
Figure 14:
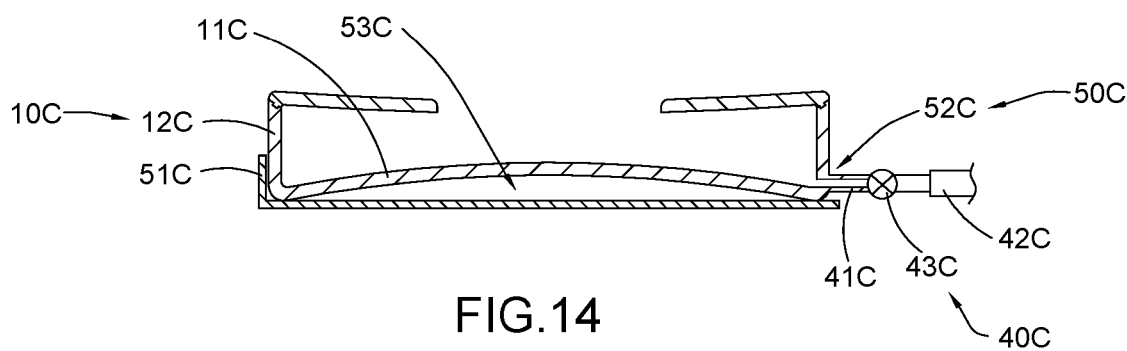
FIG. 14 is a perspective view of the urine collector according to the fifth preferred embodiment of the present invention.

Referring to FIG. 13 and FIG. 14 of the drawings, a urine collector according to a fifth embodiment illustrates an alternative mode of the first embodiment, wherein the urine collector is arranged for collecting urine for a user, especially for a special patient who is not easy to move around such as a vertebral fracture patient, a bone fracture patient, an apoplexy patients and obese patient. As shown in FIG. 13 and FIG. 14 of the drawings, the urine collector comprises a basin which comprises a collector 10C and a top cover 20C, and a urine guider 30C.

The structure of the urine collector is similar to the structures thereof in the above embodiments. The main improvement is that the urine collector in the fifth embodiment further comprises a bottom supporting base 50C installed on the bottom of the collector 10C.

Specifically, the bottom supporting base 50C comprises a base plate 54C, a base surrounding wall 51C extended upward from the base plate 54C and has a receiving cavity 53C defined by the base plate 54C and the base surrounding wall 51C. The base surrounding wall 51C has a discharge receiving gap 52C receiving the discharging port 41C of the discharging unit 40C, thereby preventing from affecting the discharging of the urine through the discharging port 41C. The diameter of the bottom supporting base 50C is slightly larger than the diameter of the collector 10C.

Preferably, the base plate 54C is thin and the height of the base surrounding wall 51C is shorter than the height of the surrounding wall 12C of the collector 10C. The bottom supporting base 50C is made of metal or plastic. The bottom supporting base 50C provides a well support force to the collector 10C, so that the urine collector is not easy to be sank into the bed and is more suitable for the bed with soft mattress, thereby the urine being quick and completely discharged from the collector 10C to the discharging unit 40C.

Figure 15:
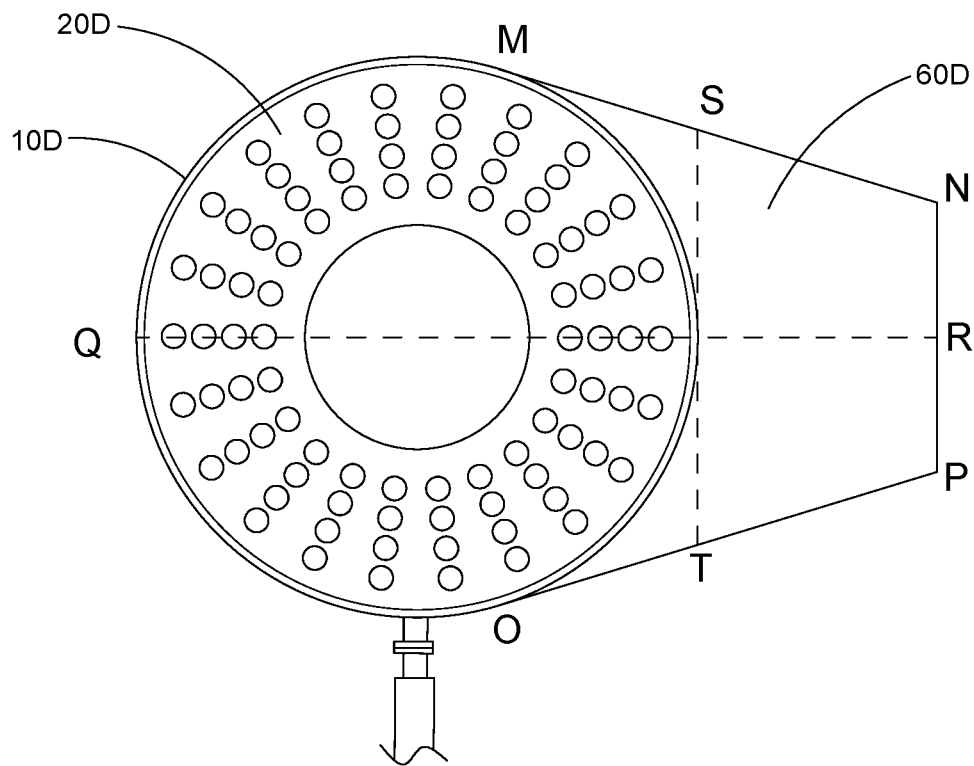
FIG. 15 is a perspective view of a urine collector according to a sixth preferred embodiment of the present invention.
Figure 16A:
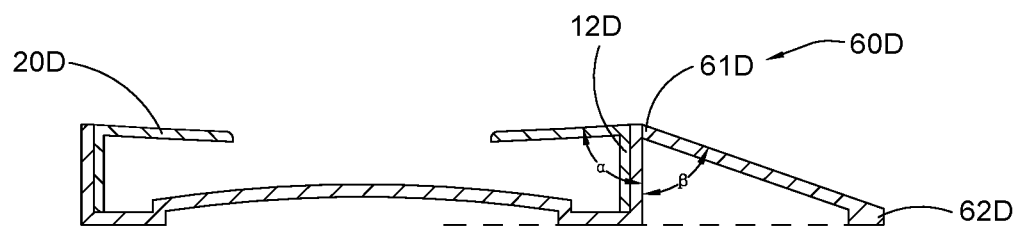
FIG. 16A is a perspective view of the urine collector according to the sixth preferred embodiment of the present invention.

Referring to FIG. 15 to FIG. 16A of the drawings, a urine collector according to a sixth embodiment illustrates an alternative mode of the first embodiment, wherein the urine collector is arranged for collecting urine for a user, especially for a special patient who is not easy to move around such as a vertebral fracture patient, a bone fracture patient, an apoplexy patients and obese patient. As shown in FIG. 15 and FIG. 16A of the drawings, the urine collector comprises a basin which comprises a collector 10D and a top cover 20D, and a urine guider 30D.

The structure of the urine collector is similar to the structures thereof in the above embodiments. The main improvement is that the urine collector in the sixth embodiment further comprises a cushioning support tail 60D extended from the collector 10D.

Specifically, the cushioning support tail 60D has an upper end 61D and a base end 62D. The collector 10D comprises a bottom wall 11D and a surrounding wall 12D upwardly extended from the bottom wall 11D to define the cavity within the bottom wall 11D and the surrounding wall 12D. The upper end 61D of the cushioning support tail 60D is aslope and outward extended from the surrounding wall 12D of the collector 10D to the base end 62D. The base end 62D is in the same horizontal surface with the bottom portion of the surrounding wall 12D. It is worth mentioning that the connection portion of the surrounding wall 12D of the collector 10D and the cushioning support tail 60D is polished to have a smooth contacting surface, so that the sharp the corner angle is removed and patients feel comfortable sitting on the urine collector.

More specifically, for example, as shown in FIG. 15 and FIG. 16A of the drawings, the line QR is in the diameter direction of the collector 10D; the line ST is vertical to the line QR and also is a tangent line of the top periphery of the surrounding wall 12D of the collector 10D; the line NP is vertical to the line ST and has a length double than the distance of the line NP to the line ST; the ling MN and the line ST are the tangent lines of the top periphery of the surrounding wall 12D of the collector 10D. The line MN, the line OP and the line NP are in the same horizontal surface. In such a manner that the inclination angle is enlarged, such as the inclination angle is changed from the angle α such as 90 degree into the angle θ such as 165 degree, so that the sharp the corner angle is removed and patients feel comfortable sitting on the urine collector, thereby reducing the harm to the lumbar.

It is worth mentioning that a layer of soft latex is affixed on the top surface of the cushioning support tail 60D so as to enhance the comfort of the urine collector.

It is worth mentioning that the cushioning support tail 60D also enhances the support force of the urine collector, as the base end 62D of the cushioning support tail 60D provides an additional supporting portions, so that the cushioning support tail 60D stably supports the collector 10D and prevents the collector 10D from sloping.

It is worth mentioning that the cushioning support tail 60D also can be used as a handle of the urine collector, so that the urine collector is easy to be moved.

Figure 16B:
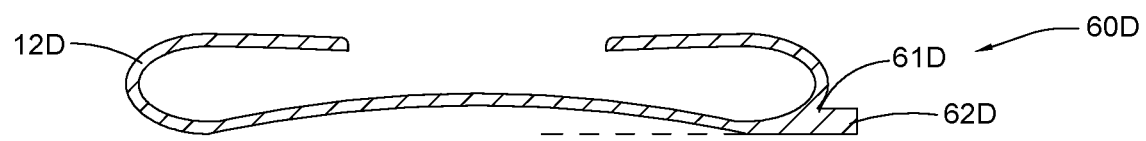
FIG. 16B is a perspective view of a urine collector illustrating an alternative mode of the sixth preferred embodiment of the present invention.
Figure 16C:
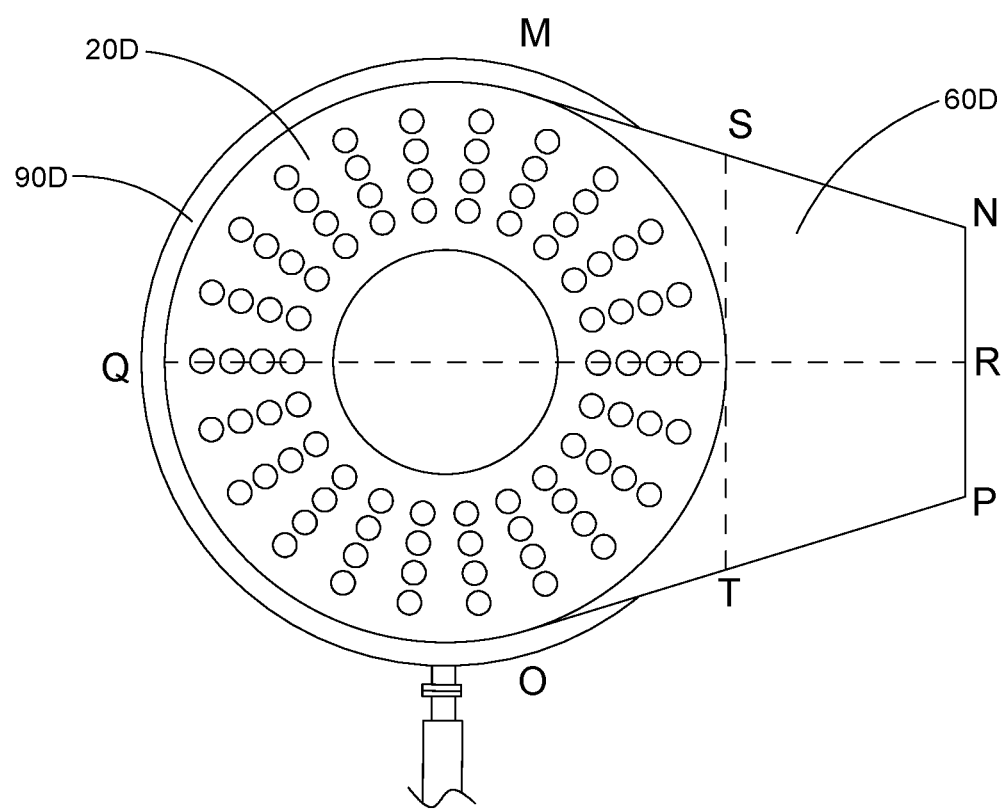
FIG. 16C is a perspective view of a urine collector illustrating an alternative mode of the sixth preferred embodiment of the present invention.

Referring to FIG. 16C of the drawings, a urine collector according to an alternative mode of the sixth embodiment is illustrated. Compared with the sixth embodiment as shown in FIG. 15 and FIG. 16A, the urine collector as shown in FIG. 16C improves the structure of the collector 10D to protect the leg of the patients. In other words, as shown in FIG. 16C of the drawings, the urine collector further comprises an extension rim 90D outward extended from the top of the surrounding wall 12D of the collector 10D so as to form a L-shape with the surrounding wall 12D, thereby enhancing the pressed area of the thighs and preventing abrasion. Preferably, the extension rim 90D has a 90 degree angle with the surrounding wall 12D of the collector 10D and has a width of about 1.5 cm.

Referring to FIG. 16B of the drawings, a urine collector according to an alternative mode of the sixth embodiment is illustrated. Compared with the sixth embodiment as shown in FIG. 15 and FIG. 16A, the urine collector as shown in FIG. 16B improves the structure of the collector 10D and the connection of the cushioning support tail 60D and the collector 10D to reduce the harm to the lumbar. In other words, as shown in FIG. 16B of the drawings, the surrounding wall 12D of the collector 10D is an arc-shaped wall, and the upper end 61D of the cushioning support tail 60D is extended from the bottom of the surrounding wall 12D and the base end 62D of the cushioning support tail 60D is horizontally and outward extended from the upper end 61D.

Figure 17:
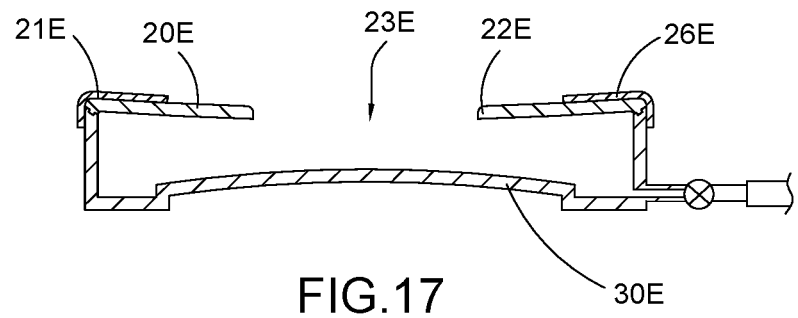
FIG. 17 is a perspective view of a urine collector according to a seventh preferred embodiment of the present invention.
Figure 18:
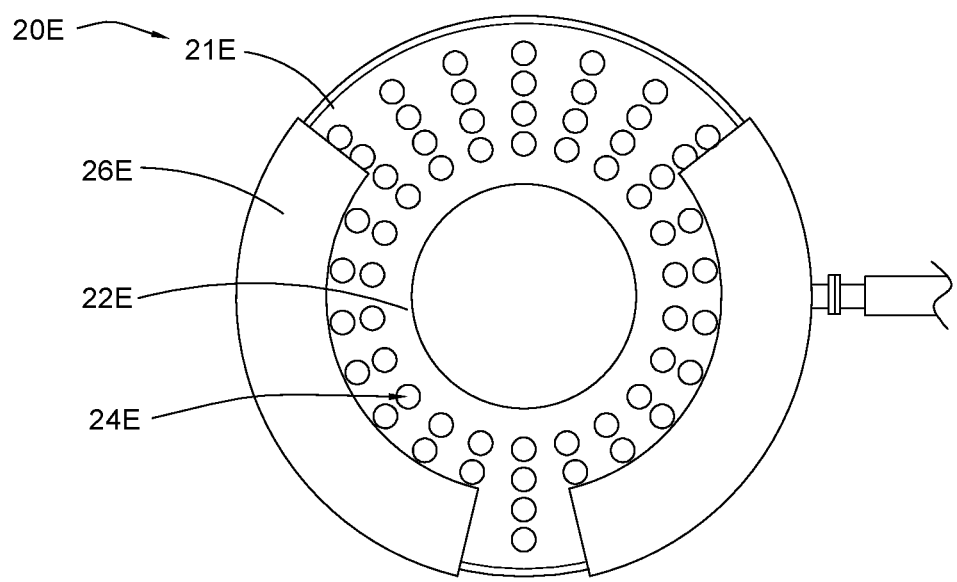
FIG. 18 is a perspective view of the urine collector according to the seventh preferred embodiment of the present invention.

Referring to FIG. 17 to FIG. 18 of the drawings, a urine collector according to a seventh embodiment illustrates an alternative mode of the first embodiment, wherein the urine collector is arranged for collecting urine for a user, especially for a special patient who is not easy to move around such as a vertebral fracture patient, a bone fracture patient, an apoplexy patients and obese patient. As shown in FIG. 17 and FIG. 18 of the drawings, the urine collector comprises a basin which comprises a collector 10E and a top cover 20E, and a urine guider 30E.

The structures of the collector 10E and the urine guider 30E are similar to the structures thereof in the above embodiments. The main improvement is the structure of the top cover 20E. The top cover 20E has a ring shape defining an outer peripheral edge 21E, an inner peripheral edge 22E, a through hole 23E within the inner peripheral edge 22E, and a plurality of urine flow holes 24E evenly arranged between the outer peripheral edge 21E and the inner peripheral edge 22E.

The top cover 20E further comprises two cushioning wings 26E attached on the outer peripheral edge 21E. Specifically, the two cushioning wings 26E are arc-shape and are symmetrically attached on the top cover 20E and correspondingly contact two hip portions, so that main hip portions of the patients are contacted with the two cushioning wings 26E. One end portion of each of the cushioning wings 26E is detachably affixed on the outer peripheral edge 21E and other end is transversely and downward extended from the outer peripheral edge 21E and along the collector 10E. The cushioning wings 26E have smooth contacting surface for the hip of the patients. Preferably, the cushioning wings 26E are made of metal, plastic or wood. The diameter of the cushioning wings 26E of the top cover 20E is slightly larger than the collector 10E. The cushioning wings 26E are easy to attach and to be cleaned. As the transverse edges of the cushioning wings 26E are smoothed, the patients feel comfortable sitting on the cushioning wings 26E.

Figure 19:
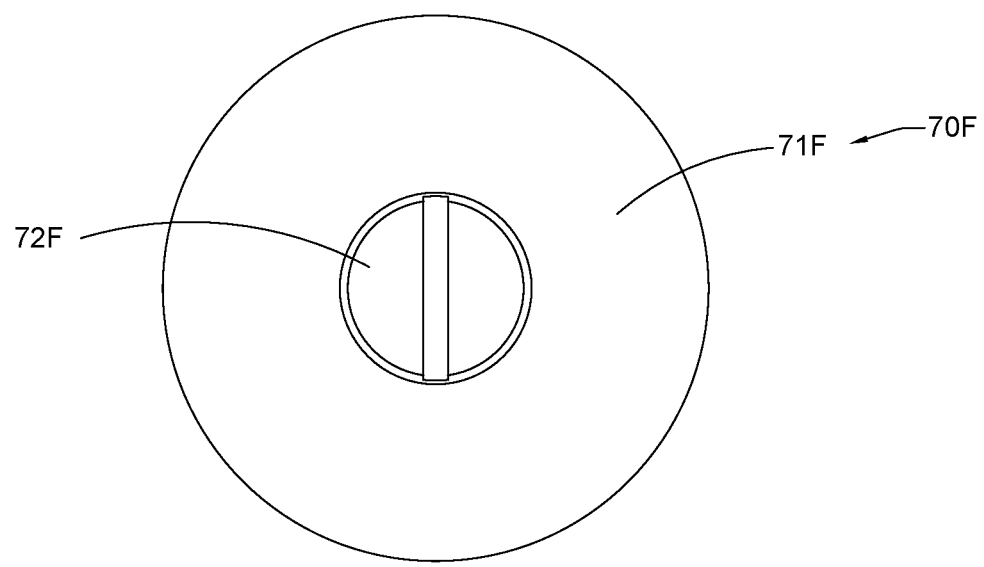
FIG. 19 is a perspective view of a urine collector according to an eighth preferred embodiment of the present invention.
Figure 20:
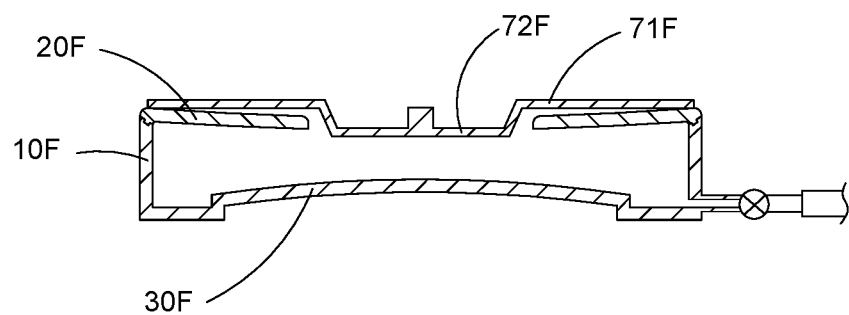
FIG. 20 is a perspective view of the urine collector according to the eighth preferred embodiment of the present invention.

Referring to FIG. 19 to FIG. 20 of the drawings, a urine collector according to a eighth embodiment illustrates an alternative mode of the first embodiment, wherein the urine collector is arranged for collecting urine for a user, especially for a special patient who is not easy to move around such as a vertebral fracture patient, a bone fracture patient, an apoplexy patients and obese patient. As shown in FIG. 19 and FIG. 20 of the drawings, the urine collector comprises a basin which comprises a collector 10F and a top cover 20F, and a urine guider 30F.

The structures of the collector 10F, the top cover 20F and the urine guider 30F are similar to the structures thereof in the above embodiments. The main improvement is that the urine collector in the eighth embodiment further comprises a top cap 70F covered on the collector 10F or the top cover 20F of the urine collector.

Specifically, the top cap 70F comprises a main cap body 71F and a concave handle 72F extended concavely from the center of the main cap body 71F. When the urine collector is not in used, the top cap 70F is covered on the collector 10F or the top cover 20F so as to protect the urine collector. The diameter of the main cap body 71F is larger than the diameter of the collector 10F. The outer portion of the concave handle 72F has a handle such that the top cap 70F is easy to be lifted. The inner portion of the concave handle 72F is protruded from the inner surface of the main cap body 71F and is received within the collector 10F or the top cover 20F, so that the top cap 70F is not easy to be slipped off from the collector 10F or the top cover 20F.

It is worth mentioning that in other embodiment, a part of the discharging unit is mounted on one side of the collector, while other part of the discharging unit is mounted on other side of the collector, so that the transporting tube has a shorter and directly way to the collector for the discharging of the urine.

It is worth mentioning that in other embodiment, two handles are respectively mounted on two sides of the collector, so that the urine collector is easy to be moved and hung.

One skilled in the art will understand that the embodiment of the present invention as shown in the drawings and described above is exemplary only and not intended to be limiting.

It will thus be seen that the objects of the present invention have been fully and effectively accomplished. The embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. A urine collector for collecting urine from a user, comprising:
    a basin which comprises a collector comprising a bottom wall and a surrounding wall upwardly extended therefrom to define a cavity and a top opening, and a top cover supported on said top opening of said collector, wherein said top cover has an outer peripheral edge detachably coupled at said surround wall and an inner peripheral edge defining a through hole within said inner peripheral edge to communicate with said cavity, wherein a tip side of said top cover is sloped downwardly from said outer peripheral edge to said inner peripheral edge, wherein said top cover comprises a plurality of urine flow holes evenly formed between said outer peripheral edge and said inner peripheral edge for guiding the urine to flow toward said urine flow holes of said top cover, and an extending support extended downwardly along said surrounding wall of said collector from said outer peripheral edge so as to support said top cover on said collector; and
    a urine guider provided at said bottom wall of said collector for collecting urine at a peripheral portion thereof for collecting the urine at said urine guider within said cavity of said collector, wherein said bottom wall of said collector further comprises an enlarge bottom base defining a circular guiding slot, and an inner concave guiding bottom extended inward and upward from said enlarge bottom base, so that said enlarge bottom base enhances a stabilization of said collector, wherein said urine guider is provided at said inner concave guiding bottom.

2. The urine collector, as recited in claim 1, wherein a diameter of said outer peripheral edge of said top cover is slight smaller than a diameter of said collector.

3. The urine collector, as recited in claim 1, wherein said extending support of said top cover has three extending supporting legs spacedly arranged with each other.

4. The urine collector, as recited in claim 1, wherein said extending support is contacted with an inner surface of said surrounding wall.

5. The urine collector, as recited in claim 1, wherein said extending support is contacted with an outer surface of said surrounding wall.

6. A urine collector for collecting urine from a user, comprising:
    a basin which comprises a collector comprising a bottom wall and a surrounding wall upwardly extended therefrom to define a cavity and a top opening, and a top cover supported on said top opening of said collector;
    a urine guider provided at said bottom wall of said collector for collecting urine at a peripheral portion thereof for collecting the urine at said urine guider within said cavity of said collector, wherein said bottom wall of said collector further comprises an enlarge bottom base defining a circular guiding slot, and an inner concave guiding bottom extended inward and upward from said enlarge bottom base, so that said enlarge bottom base enhances a stabilization of said collector, wherein said urine guider is provided at said inner concave guiding bottom;
    a bottom supporting base installed on said bottom of said collector so as to enhance a stabilization of said collector, wherein said bottom supporting base comprises a base plate, a base surrounding wall extended upward from said base plate and has a receiving cavity defined by said base plate and said base surrounding wall; and
    a discharging unit operatively connected with said urine guider, wherein said discharging unit comprises a discharging port formed at said basin to communicate with said urine guider and a transporting tube detachably coupled at said discharging port for discharging the urine at said urine guider through said discharging port, wherein said base surrounding wall has a discharge receiving gap receiving said discharging port of said discharging unit.

7. A urine collector for collecting urine from a user, comprising:
    a basin which comprises a collector comprising a bottom wall and a surrounding wall upwardly extended therefrom to define a cavity and a top opening, and a top cover supported on said top opening of said collector;
    a urine guider provided at said bottom wall of said collector for collecting urine at a peripheral portion thereof for collecting the urine at said urine guider within said cavity of said collector, wherein said bottom wall of said collector further comprises an enlarge bottom base defining a circular guiding slot, and an inner concave guiding bottom extended inward and upward from said enlarge bottom base, so that said enlarge bottom base enhances a stabilization of said collector, wherein said urine guider is provided at said inner concave guiding bottom; and
    a cushioning support tail extended outwardly from said collector so as to enhance a stabilization of said collector and to provide a cushioning effect, wherein said cushioning support tail has a smooth contacting surface and is affixed with a layer of soft latex on said top surface of said cushioning support tail.

8. A urine collector for collecting urine from a user, comprising:
    a basin which comprises a collector comprising a bottom wall and a surrounding wall upwardly extended therefrom to define a cavity and a top opening, and a top cover supported on said top opening of said collector;
    a urine guider provided at said bottom wall of said collector for collecting urine at a peripheral portion thereof for collecting the urine at said urine guider within said cavity of said collector, wherein said bottom wall of said collector further comprises an enlarge bottom base defining a circular guiding slot, and an inner concave guiding bottom extended inward and upward from said enlarge bottom base, so that said enlarge bottom base enhances a stabilization of said collector, wherein said urine guider is provided at said inner concave guiding bottom; and a top cap covered on said basin, wherein said top cap comprises a main cap body and a concave handle extended concavely from the center of said main cap body, wherein a diameter of said main cap body is larger than a diameter of said collector.

* * * * *